US00PP32135P2

(12) United States Plant Patent
Horvath

(10) Patent No.: US PP32,135 P2
(45) Date of Patent: Aug. 25, 2020

(54) ***SEDUM* PLANT NAMED 'LIME JOY'**

(50) Latin Name: ***Sedum* hybrid**
Varietal Denomination: Lime Joy

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 0 days.

(21) Appl. No.: 16/501,167

(22) Filed: Mar. 4, 2019

(51) Int. Cl.
*A01H 5/12* (2018.01)
*A01H 6/32* (2018.01)

(52) U.S. Cl.
USPC ..... Plt./479

(58) Field of Classification Search
USPC ..... Plt./479
See application file for complete search history.

*Primary Examiner* — Susan McCormick Ewoldt

(57) ABSTRACT

A new, distinct *Sedum* plant as illustrated and described, characterized by larger grey green foliage, deep pink bi-color flowers, taller height, extra number of flowers per stem, and a upright mounding habit.

2 Drawing Sheets

Figure 1:
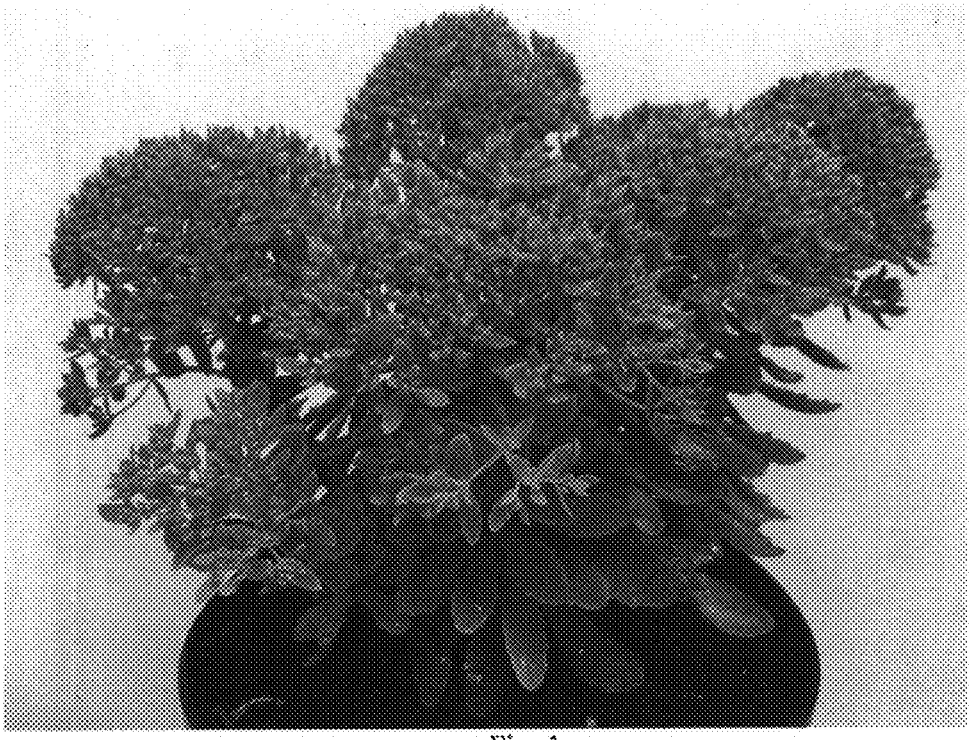

Latin name: *Sedum* hybrid.
Cultivar name: 'Lime Joy'.

BACKGROUND OF THE INVENTION

The present invention relates to a new and distinct hybrid of *Sedum* plant named 'Lime Joy' characterized by larger grey green foliage, deeper pink bi-color flowers, taller height, extra number of flowers per stem, and an upright mounding habit compared to the seed parent. The new *Sedum* was raised as a seedling from open pollinated seed, of the female parent, an unnamed *Sedum tatarinowii*, in Hebron, Ill. in 2017. The selection of the new plant was due to its' larger grey green foliage, deeper pink bi-color flowers, taller height, extra number of flowers per stem, and an upright mounding habit compared to the seed parent. Initial asexual reproduction has taken place at a nursery in Hebron, Ill. since 2018 by means of division, and vegetative cuttings. The new *Sedum* has shown to be stable and identical in reproduction to the originally discovered plant after rooting over 300 plants from 2017 to 2018. No plants of the new *Sedum* have been sold in this country, or anywhere in the world, prior to the filing of this application, nor has any disclosure of the new plant been made prior to the filing of this application with the exception of that which was disclosed by the inventor and his company, Intrinsic Perennial Gardens, Inc within one year of filing of this application and was derived directly from the inventor.

SUMMARY OF THE INVENTION

The new *Sedum* plant named 'Lime Joy' characterized by larger grey green foliage, deep pink bi-color flowers, taller height, extra number of flowers per stem, and a upright mounding habit compared to the seed parent have been observed to be unique and stable.

Plants of the new *Sedum* can be compared plants of *Sedum spectabile* 'Neon' not patented. 1. The new *Sedum* plant is a hybrid and does not produce seed while *Sedum spectabile* 'Neon' is fertile and produces seed. 2. The new *Sedum* has deep pink bi-color flowers while *Sedum spectabile* 'Neon' is entirely pink.

Plants of the new *Sedum* can also be compared to the seed parent plant *Sedum tatarinowii*, not patented. 1. The new plant is a hybrid and does not produce seed while the seed parent plant is fertile and produces viable seed. 2. The new *Sedum* has a mature size of 23 cm high and 46 cm wide while the seed parent has a mature size of 12 cm high and 30 cm wide. 3. The new *Sedum* has larger foliage measuring on average up to 7 cm long by 2 cm wide while the seed parent has foliage measuring 6 mm across by 2 cm long. 4. The new *Sedum* has a stem diameter of 7 mm while the seed parent has stem diameter of 3 mm. 5. The new *Sedum* has deep pink bi-color flowers, compared to the mostly white flowers of the seed parent.

Plants of the new *Sedum* can also be compared to *Sedum* 'Pure Joy' U.S. Plant Pat. No. 24,194. The main difference being the flower color on the new *Sedum* has deep pink bi-color flowers with an overall appearance of N74 A, with petals colored 73 A and carpels colored N66 A, compared to the light pink flowers with overall flower color 62 C of the *Sedum* 'Pure Joy'.

DESCRIPTION OF PHOTOGRAPHS

Figure 2:
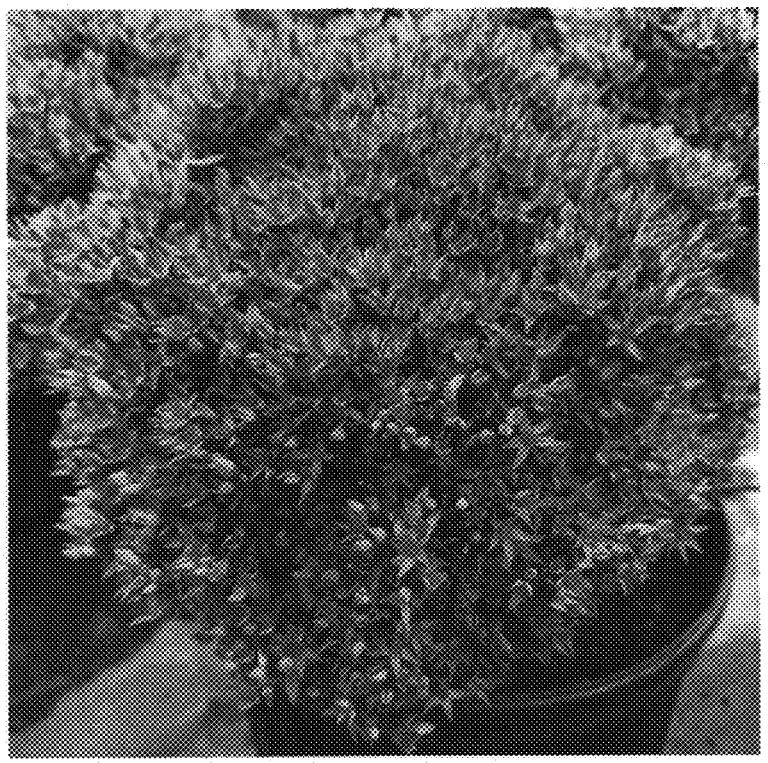
Figure 3:
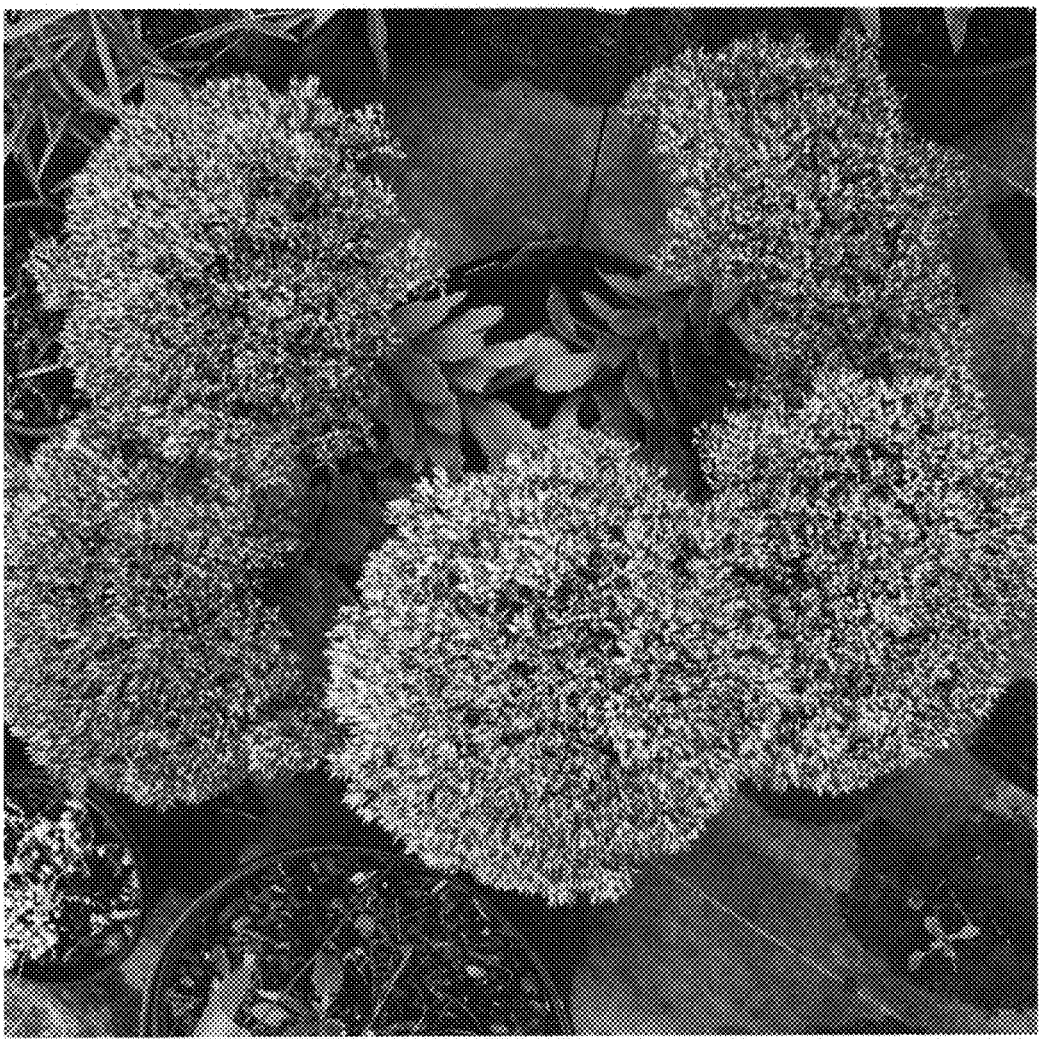

Plants pictured in the drawing were grown for one year.
FIG. 1. The plant shown in bud, in July.
FIG. 2. Close up of the flower.
FIG. 3 A single plant in September.

DETAILED BOTANICAL DESCRIPTION

In the following description, color references are made to The Royal Horticultural Society Colour Chart (2001). Plants used for the description were grown for two years at a nursery in Hebron, Ill. USA. Measurements and numerical values represent averages of typical plants.

Botanical classification: *Sedum* hybrid cultivar 'Lime Joy'.

Parentage: Male or pollen parent is unknown and the female or seed parent is an unnamed *Sedum tatarinowii*.

Propagation: Vegetative division and cutting propagation. Roots initiate in about 15 days.

Rooting habit: Round, fibrous and shallow. Root Color—163 D.

Plant description: Overall habit of the new *Sedum* is basal clumps, with upright stems topped by deep pink bi-color flowers in August and September. Growth of the new *Sedum* is vigorous.

*Plant type*.—Herbaceous perennial.
*Plant height*.—Average 23 cm.
*Plant width*.—Up to 46 cm.
*Stem color*.—146 C.
*Stem shape*.—Both typical and observed — round.
*Stem texture*.—Glabrous.
*Stem length*.—20 cm.
*Stem diameter*.—12 mm.
*Internode length*.—8-10 mm.

Foliage:

*Type*.—Deciduous.
*Branching habit*.—Numerous, basal.
*Shape*.—Obovate.
*Leaf division*.—Simple.
*Petiole*.—None.
*Length*.—40-50 mm.
*Width*.—16 mm.
*Thickness*.—2 mm.
*Margin*.—Dentate.
*Leaf apex*.—Typical and observed — obtuse.
*Leaf bases*.—Typical and observed — cuneate.
*Texture*.—Smooth, glabrous on both Adaxial and Abaxial surface.
*Leaf arrangement*.—Alternate, crowded except at the base of the stems.
*Leaf venation pattern*.—None noticed.
*Leaf vein color*.—None noticed.
*Adaxial leaf description*.—Color is 146 A.
*Abaxial leaf description*.—Color is 146 B.
*Fall foliage color*.—None noticed.

Flower:

*Petal count*.—5.
*Petal shape*.—Lanceolate.
*Individual flower*.—Shape — stellate. Individual size — 12 mm wide and 6 mm length.
*Adaxial petal color*.—73 A, next to carpels colored N66 A making the overall flower bi-color.
*Abaxial petal color*.—73 C.
*Petal apex shape*.—Acuminate.
*Petal base*.—3 mm wide.
*Petal texture*.—Glabrous on both Adaxial and Abaxial surface.
*Petal length*.—5 mm and width — 3 mm.
*Petal margin*.—Typical and observed — entire.
*Petal bases*.—Typical and observed — obtuse.
*Inflorescence type*.—Panicle on basal flowering stems.
*Panicle color*.—As a whole the color is close to N66 B.
*Inflorescence size*.—17 cm across, 7 mm tall.
*Inflorescence length*.—7 mm and. width — 15 cm.
*Flower number*.—Approximately 1200 per panicle.
*Bloom period and duration*.—Mid August to mid September, lasting 3-5 weeks.
*Bud shape typical and observed*.—Elliptical.
*Bud length*.—Typical and observed — 7 mm.
*Bud diameter*.—Typical and observed — 3 mm.
*Bud color*.—Typical and observed — close to 146 B.
*Bud texture*.—Glabrous.
*Sepal size*.—5 mm across, 10 mm tall.
*Sepal number*.—5.
*Sepal shape*.—Typical and observed — narrow ovate.
*Sepal base*.—Typical and observed — cordate, Texture — glabrous.
*Sepal apex*.—Typical and observed — acute.
*Sepal margin*.—Typical and observed — entire.
*Sepal color*.—Abaxial and adaxial typical and observed — 146 A.
*Peduncle length*.—Typical and observed — 11 mm.
*Peduncle shape*.—Round, Texture — glabrous.
*Peduncle diameter*.—Typical and observed — 2-3 mm.
*Peduncle color*.—Typical and observed — close to 146 D.
*Pedicel length*.—Typical and observed — 6 mm.
*Pedicel diameter*.—Typical and observed — 1 mm.
*Pedicel color*.—Typical and observed — close to 146 D.
*Pedicel shape*.—Round, Texture — glabrous.
*Carpel color*.—N66 A throughout.
*Carpel surfaces*.—Glabrous.
*Stigma shape*.—Capitate.
*Stigma size*.—2-3 mm.
*Style length*.—2 mm and shape — slender.
*Ovary size*.—1-2 mm and shape — cordate.
*Fertility*.—Sterile, 10 anthers with little pollen, 10 stamens at 7 mm long.
*Anther color*.—Close to N79 C, Pollen color — close to N155 A.
*Blooming habit*.—Domed, terminal panicle on up to 46 cm stems.
*Scent*.—No scent noticed.
*Fruit*.—None.
*Hardiness*.—U.S.D.A. hardiness zones 4-9.
*Disease resistance*.—Resistance to diseases common to *Sedum* has not been observed on plants grown under nursery conditions. Pest Resistance — Resistance to pests common to *Sedum* has not been observed on plants grown under nursery conditions.

I claim:

1. A new, distinct *Sedum* plant as illustrated and described, characterized by larger grey green foliage, deep pink bi-color flowers, taller height, extra number of flowers per stem, and a upright mounding habit compared to the seed parent.

* * * * *